(12) United States Patent
Weibel et al.

(10) Patent No.: US 9,282,738 B2
(45) Date of Patent: Mar. 15, 2016

(54) ANTIMICROBIAL COMPOSITIONS AND METHODS OF USE THEREOF

(75) Inventors: Douglas B. Weibel, Madison, WI (US); Ye Jin Eun, Madison, WI (US); Maoquan Zhou, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 739 days.

(21) Appl. No.: 13/546,667

(22) Filed: Jul. 11, 2012

(65) Prior Publication Data
US 2013/0018079 A1 Jan. 17, 2013

Related U.S. Application Data

(60) Provisional application No. 61/506,294, filed on Jul. 11, 2011.

(51) Int. Cl.
| | |
|---|---|
| *A61K 31/15* | (2006.01) |
| *A61K 31/40* | (2006.01) |
| *A61K 31/4164* | (2006.01) |
| *A61K 31/421* | (2006.01) |
| *A61K 31/426* | (2006.01) |
| *A01N 43/52* | (2006.01) |
| *A61K 31/4184* | (2006.01) |
| *A61K 45/06* | (2006.01) |
| *C07D 235/08* | (2006.01) |
| *C07D 235/10* | (2006.01) |

(52) U.S. Cl.
CPC ............... *A01N 43/52* (2013.01); *A61K 31/15* (2013.01); *A61K 31/40* (2013.01); *A61K 31/4164* (2013.01); *A61K 31/4184* (2013.01); *A61K 31/421* (2013.01); *A61K 31/426* (2013.01); *A61K 45/06* (2013.01); *C07D 235/08* (2013.01); *C07D 235/10* (2013.01)

(58) Field of Classification Search
CPC .................................................. A61K 31/4164
See application file for complete search history.

(56) References Cited

U.S. PATENT DOCUMENTS

2010/0273837 A1  10/2010  Haydon et al.

FOREIGN PATENT DOCUMENTS

| WO | 2004062674 A2 | 7/2004 |
| WO | 2005007162 A1 | 1/2005 |
| WO | 2008141012 A2 | 11/2008 |
| WO | 2010054102 A2 | 5/2010 |
| WO | 2011075136 A1 | 6/2011 |

OTHER PUBLICATIONS

El-masry et al. ("Synthesis and Antimicrobial Activity of Some New Benzimidazole Derivatives" Molecules, 2000, 5, 1429-1438).*
Nelson, Mark L; Modulation of Antibiotic Efflux in Bacteria; Curr. Med. Chem.—Anti-Infective Agents; 1; pp. 35-54; (2002).
Piddock, Laura J. V.; "Clinical Relevant Chromosomally Encoded Multidrug Resistance Efflux Pumps in Bacteria"; Clinical Microbiology Reviews; pp. 382-402; (2006).
Lomovskaya et al.; "Identification and Characterization of Inhibitors of Multidrug Resistance Efflux Pumps in Pseudomonas aeruginosa: Novel Agents for Combinatoin Therapy"; Antimicrobial Agents and Chemotherapy; pp. 105-116; (2001).
Haydon et al.; "An Inhibitor of FtsZ with Potent and Selective Anti-Staphylococcal Activity"; Science; 32; pp. 1673-1675; (2008).
Zhou et al.; "Structure-Activity Studies of Divin: An Inhibitor of Bacterial Cell Division"; ACS Med. Chem. Lett., 2013, 4(9), pp. 880-885; Publication Date (Web): Jul. 29, 2013 (Letter) DOI: 10.1021/ml400234x.

* cited by examiner

*Primary Examiner* — Yong Chong
(74) *Attorney, Agent, or Firm* — Cantor Colburn LLP

(57) ABSTRACT

Described herein is a novel class of inhibitors of bacterial cell division. Several lines of evidence suggest the compounds disclosed herein specifically target the division process and have antibacterial activity in vitro and in vivo. The inhibitors are useful for treating subject in need of treatment for bacterial infections as will as for inhibiting bacterial growth, such as growth on contaminated surfaces.

26 Claims, 8 Drawing Sheets

Division plane assembly
FtsZ-GFP (green)

1. In vitro ATPase assay using fluorescence polarization

2. In vivo microscopy assay using a MipZ-YFP strain

Inset: DMSO treated controls
Scale bar = 5 μm
C. crescentus CB15N
5 μM Compound 1, 11 hr treatment Inset: DMSO treated controls
Scale bar = 5 μm
E. coli ΔtolC
50 μM Compound 1, 12 hr treatment

A

Single-letter labels represent names of Fts proteins (e.g. Z = FtsZ)

B  DMSO     Compound 1
                8 hr, 5 μM

C

DMSO
Compound 1

For each sample, 18 - 124 cells were counted.
*** represents $p<0.001$
** represents $p<0.01$
* represents $p<0.05$

ANTIMICROBIAL COMPOSITIONS AND METHODS OF USE THEREOF

CROSS-REFERENCE TO RELATED APPLICATIONS

This application claims priority to U.S. Provisional Application No. 61/506,294 filed on Jul. 11, 2011, which is incorporated herein by reference in its entirety.

STATEMENT REGARDING FEDERALLY SPONSORED RESEARCH & DEVELOPMENT

This invention was made with government support under 11-CRHF-0-6055 awarded by the USDA/NIFA. The government has certain rights in the invention.

FIELD OF THE DISCLOSURE

The present disclosure is related to novel inhibitors of bacterial cell division, and methods of use of the inhibitors.

BACKGROUND

In the past two decades, significant progress has been made towards understanding the mechanistic complexity of bacterial cell division. Once viewed as a simple binary fission, it is now known that cell division in bacteria involves a tubulin homolog, FtsZ. FtsZ polymers initiate cell division and recruit downstream machinery for subsequent remodeling of the cell wall. Since FtsZ and the associated machinery plays a central role in forming the septum, several mechanisms exist to regulate its polymerization in both space and time. Perturbing the function of the components of this machinery directly, or the regulatory processes on cell division, has become an attractive route for antibiotic discovery and development.

U.S. Patent Publication 2010/0273837, for example, discloses substituted thiadiazolylmethoxybenzamide or thiadiazolylmethoxypyridylamides with some inhibitory activity against *Staphylococcus aureus*, a Gram-positive pathogen. A specific compound that has been tested is PC190723, a compound identified by systematic modification of 3-methoxybenzamide. PC190723 was shown to protect mice from a normally lethal dose of the MRSA strain of *Staphylococcus aureus*.

What is needed are additional inhibitors of cell division with antimicrobial activity, particularly inhibitors effective against a variety of microorganisms.

BRIEF SUMMARY

In one aspect, a pharmaceutical composition comprises a cell division inhibitor and a pharmaceutically acceptable excipient, wherein the cell division inhibitor is of Formula I or a pharmaceutically acceptable salt thereof:

G-Q-Y—Z—Ar     (I)

wherein
G is

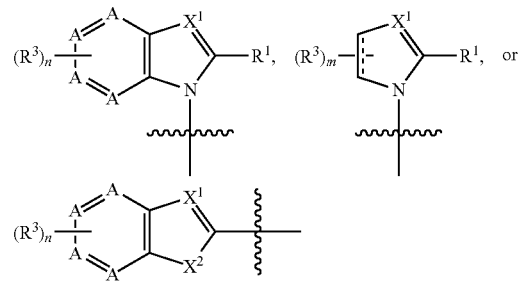

wherein each instance of A is independently CH or N provided that the total number of N is 0 or 1;
$R^1$ is hydrogen, hydroxy, amino, halogen, cyano, $C_1$-$C_6$alkyl, $C_1$-$C_6$alkoxy, $C_1$-$C_6$haloalkyl, $C_1$-$C_6$haloalkoxy, aryl, or (aryl)alkyl;
$X^1$ is N, $CR^2$, O, or S;
$X^2$ is O, S, or $NR^4$;
$R^2$ is hydrogen, $C_1$-$C_6$alkyl, $C_1$-$C_6$alkoxy, $C_1$-$C_6$haloalkyl, $C_1$-$C_6$haloalkoxy, aryl, or (aryl)alkyl;
each instance of $R^3$ independently is hydroxy, sulfate, nitro, amino, halogen, cyano, $C_1$-$C_4$alkyl, $C_1$-$C_4$alkoxy, $C_3$-$C_7$cycloalkyl, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, phenyl, pyridyl, heterocycloalkyl, alkylcarboxamide, $C_2$-$C_4$alkenyl, or $C_2$-$C_4$alkynyl;
n is 0, 1, or 2;
m is 0 or 1;
Q is a bond or a $C_1$-$C_6$ hydrocarbon linking group comprising 0, 1, or 2 heteroatoms chosen from O, S, or $NR^4$, and wherein the linking group is substituted by 0, 1, 2, or 3 substituents independently chosen from hydroxy, sulfate, nitro, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, or oxo;
$R^4$ is hydrogen, $C_1$-$C_6$alkyl, or $C_1$-$C_6$haloalkyl;
Y is —(C=O)NH—N=CH—,
—(C=O)NH—,
—NH(C=O)—,
—(C=O)O—,
—O(C=O)—
—O(C=O)O—,
—NH(C=O)NH—,
—NH(C=O)O—,
—O(C=O)NH—
or
—(C=O)—;
Z is a bond or a $C_1$-$C_3$ hydrocarbon linking group comprising 0, 1, or 2 heteroatoms chosen from O, S, or $NR^4$, and wherein the linking group is substituted by 0, 1, 2, or 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, or oxo;
Ar is aryl or heteroaryl, substituted with 0, 1, 2, or 3 substituents independently chosen from hydroxy, sulfate, nitro, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_2$-$C_6$alkanoyl, C₁-C2haloalkyl, C₁-C₂haloalkoxy, phenyl, pyridyl, heterocycloalkyl, alkylcarboxamide, C₂-C4alkenyl, or C₂-C₄alkynyl, and the dashed line in the G structures is a single or double bond.

In another aspect, a method of treating a subject in need of treatment for a bacterial infection, comprises administering to the subject an effective amount of a cell division inhibitor as defined above.

In yet another aspect, a method of inhibiting bacterial growth comprises contacting the bacteria with a cell division inhibitor as defined above in an amount sufficient to inhibit bacterial growth.

The above-described and other features will be appreciated and understood by those skilled in the art from the following detailed description, drawings, and appended claims.

DETAILED DESCRIPTION

Described herein are novel inhibitors of cell division and their use to treat bacterial infections. Bacterial cells reproduce by coordinating growth, DNA replication, and division into two daughter cells. The physical separation of two cells involves a bacterial tubulin homolog FtsZ. Without being held to theory, it is believed that FtsZ polymers work together to provide a constricting force in a dividing cell and also serve as a scaffold to recruit other proteins necessary for division.

Figure 1:
FIG. 1 shows the in vivo localization of FtsZ-GFP at the division plane and a schematic of FtsZ assembly and the concentration gradient of MipZ which concentrates FtsZ assembly at the division plane in *Caulobacter crescentus*.
Figure 1:
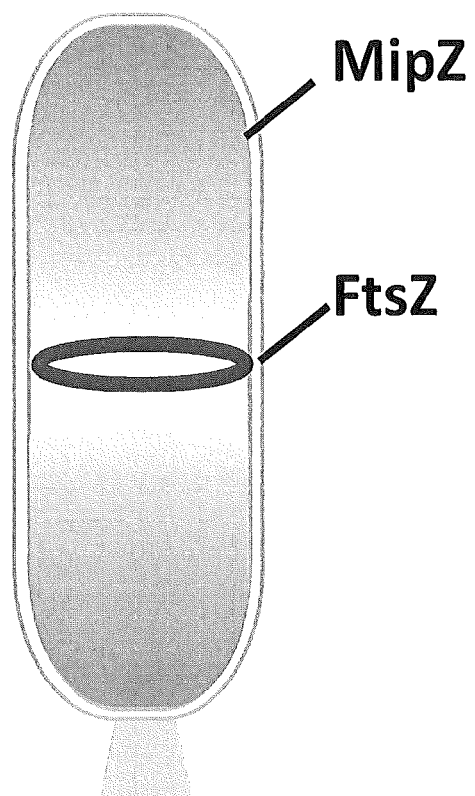
Figure 2:
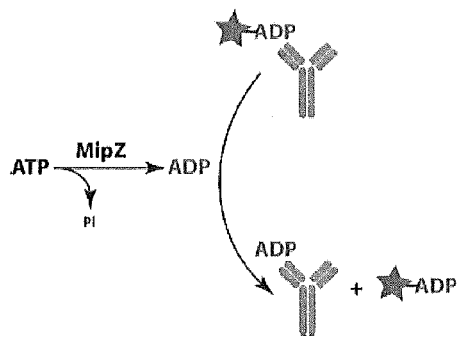
FIG. 2 is a schematic of the assay used to identify inhibitors of MipZ.
Figure 2:
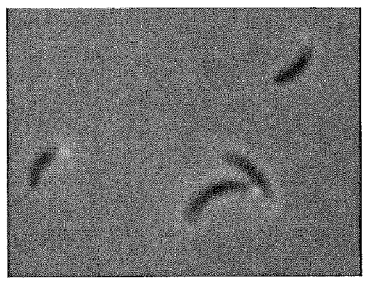

In *C. crescentus* cells, the mechanism of accurately placing FtsZ in time and space in the cell involves an ATPase, MipZ. (FIG. 1) The ATP-bound form of MipZ promotes depolymerization of FtsZ filaments by increasing the GTP hydrolysis rate of FtsZ. In addition to its inhibition of FtsZ, MipZ binds to nucleoproteins near the origin of the chromosome and establishes an asymmetric polar gradient. The gradient becomes bipolar (i.e., symmetric) when the cell undergoes chromosome replication to place two origins at opposite poles. This bipolar gradient of MipZ positions the division at the mid-cell: FtsZ is localized at the mid-cell, where the concentration of the inhibitory gradient of MipZ is the lowest. Thus, MipZ coordinates chromosome segregation and the onset of cell division both spatially and temporally such that FtsZ assembles at the mid-cell after the segregation of the chromosomes. Because of the relationship between FtsZ and MipZ, a coupling assay and a fluorescence polarization assay of MipZ ATPase activity were used to screen compounds for their ability to inhibit cell division. (FIG. 2)

From a high-throughput screen at the Keck Small Molecule Facility at the University of Wisconsin, a small molecule inhibitor of cell division in the model bacterium *Caulobacter crescentus*, compound 1, was identified. The compound is toxic to *C. crescentus* and has a minimum inhibitory concentration of 5 μM. Compound 1 and its analogs are a new class of antimicrobial compounds.

Several lines of evidence suggest that compound 1 and its analogs inhibit cell division specifically: 1) Cells treated with compound 1 exhibit a cell division defect similar to mutant cells that overexpress FtsZ. 2) The overexpression of an inhibitor of FtsZ polymerization (MipZ) inhibits the initiation of division and causes cells to grow into long filaments. The addition of compound 1 relieves this phenotype by making it possible for cells to divide in the presence of excess MipZ. 3) Knocking out a protein (ZapA) that stabilizes FtsZ causes cell division to occur at random positions along the cell and leads to an increase in the average and standard deviation of cell length. Treating the knock-out strain with compound 1 attenuates this increase and returns the cell length distribution back to normal. 4) Treatment with compound 1 caused incomplete constrictions in dividing cells of *C. crescentus* and *E. coli*, although cells resume and finish the division process when the compound is washed away. 5) Compound 1 perturbs the localization of several fluorescently tagged Fts proteins, including FtsB, FtsL, FtsI, and FtsK. The perturbation in the assembly of division proteins was also observed in *E. coli* cells.

Compound 1 has the following structure:

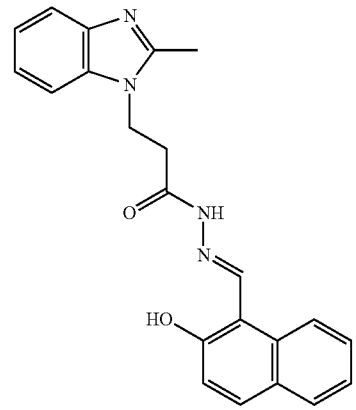 [SMILES: Cc1nc2ccccc2n1CCC(=O)N/N=C/c1c(O)ccc2ccccc12]

In one embodiment, the cell division inhibitor includes compounds and pharmaceutically acceptable salts of Formula I:

G-Q-Y—Z—Ar     (I)

wherein
G is

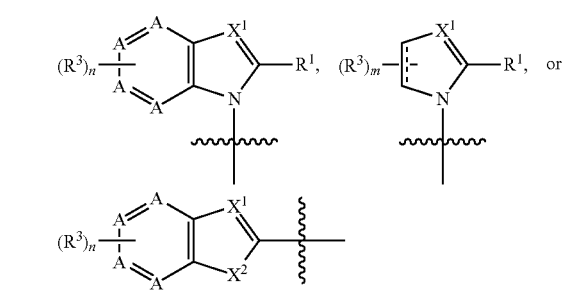

wherein each instance of A is independently CH or N provided that the total number of N is 0 or 1;

$R^1$ is hydrogen, hydroxy, amino, halogen, cyano, $C_1$-$C_6$alkyl, $C_1$-$C_6$alkoxy, $C_1$-$C_6$haloalkyl, $C_1$-$C_6$haloalkoxy, aryl, or (aryl)alkyl;

$X^1$ is N, $CR^2$, O, or S;

$X^2$ is O, S, or $NR^4$;

$R^2$ is hydrogen, $C_1$-$C_6$alkyl, $C_1$-$C_6$alkoxy, $C_1$-$C_6$haloalkyl, $C_1$-$C_6$haloalkoxy, aryl, or (aryl)alkyl;

each instance of $R^3$ independently is hydroxy, sulfate, nitro, amino, halogen, cyano, $C_1$-C4alkyl, $C_1$-$C_4$alkoxy, $C_3$-$C_7$cycloalkyl, mono- and di-($C_1$-$C_4$alkyDamino, $C_2$-$C_6$alkoxycarbonyl, $C_2$-$C_6$alkanoyl, $C_1$-$C_2$haloalkyl, $C_1$-$C_2$haloalkoxy, phenyl, pyridyl, heterocycloalkyl, alkylcarboxamide, $C_2$-$C_4$alkenyl, or $C_2$-$C_4$alkynyl;

n is 0, 1, or 2;

m is 0 or 1;

Q is a bond or a $C_1$-$C_6$ hydrocarbon linking group comprising 0, 1, or 2 heteroatoms chosen from O, S, or $NR^4$, and wherein the linking group is substituted by 0, 1, 2, or 3 substituents independently chosen from hydroxy, sulfate, nitro, amino, cyano, halogen, $C_1$-$C_4$alkyl, $C_3$-$C_7$cycloalkyl, $C_1$-$C_4$alkoxy, mono- and di-($C_1$-$C_4$alkyl)amino, C2-$C_6$alkoxycarbonyl, $C_2$-$C_6$alkanoyl, $C_1$-$C_2$haloalkyl, $C_1$-$C_2$haloalkoxy, or oxo;

$R^4$ is hydrogen, $C_1$-$C_6$alkyl, or $C_1$-$C_6$haloalkyl;

Y is —(C═O)NH—N═CH—,
—(C═O)NH—,
—NH(C═O)—,
—(C═O)O—,
—O(C═O)—
—O(C═O)O—,
—NH(C═O)NH—,
—NH(C═O)O—,
—O(C═O)NH—
or
—(C═O)—;

Z is a bond or a $C_1$-$C_3$ hydrocarbon linking group comprising 0, 1, or 2 heteroatoms chosen from O, S, or $NR^4$, and wherein the linking group is substituted by 0, 1, 2, or 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, or oxo;

Ar is aryl or heteroaryl, substituted with 0, 1, 2, or 3 substituents independently chosen from hydroxy, sulfate, nitro, amino, cyano, halogen, $C_1$-$C_4$alkyl, $C_3$-$C_7$cycloalkyl, $C_1$-C4alkoxy, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, phenyl, pyridyl, heterocycloalkyl, alkylcarboxamide, $C_2$-$C_4$alkenyl, or $C_2$-$C_4$alkynyl; and the dashed line in the G structures is a single or double bond.

Within this embodiment, $R^1$ is hydrogen, fluoro, $C_1$-$C_3$alkyl, $C_1$-$C_3$alkoxy, $C_1$-C3haloalkyl (e.g. fluoroalkyl), $C_1$-$C_3$haloalkoxy, or aryl, more specifically $R^1$ is hydrogen, $C_1$-C2alkyl, $C_1$-$C_2$alkoxy, $C_1$-$C_2$haloalkyl, or $C_1$-$C_2$haloalkoxy, and yet more specifically $R^1$ is methyl or trifluoromethyl.

Further within this embodiment, $X^1$ is N.

Still further within this embodiment, each instance of $R^3$ independently is hydroxy, sulfate, nitro, halogen, $C_1$-$C_2$alkyl, $C_1$-$C_2$alkoxy, $C_3$-$O_5$cycloalkyl, mono- and di-(C1-C2alkyl)amino, $C_2$-$C_4$alkoxycarbonyl, $C_1$-$C_2$haloalkyl, or $C_1$-$C_2$haloalkoxy.

Within this embodiment Q is a $C_1$-$C_3$ hydrocarbon linking group substituted by 0, 1, 2, or 3 substituents independently chosen from hydroxy, amino, halogen (specifically fluoro), $C_1$-$C_2$alkyl, $C_3$-$O_5$cycloalkyl, $C_1$-$C_2$alkoxy, mono- and di-($C_1$-$C_2$alkyl)amino, $C_2$-$C_4$alkoxycarbonyl, $C_1$-$C_2$haloalkyl (specifically fluoroalkyl), $C_1$-$C_2$haloalkoxy (specifically fluoroalkoxy), or oxo.

Further within this embodiment, Y is —(C═O)NH-N═CH—,

—(C═O)NH—,

—NH(C═O)NH—,

—NH(C═O)O—, or

—O(C═O)NH—.

Also within this embodiment, Z is a bond.

Furthermore, within this embodiment, Ar is aryl substituted with 1 or 2 substituents independently chosen from hydroxy, amino, cyano, halogen (specifically fluoro), $C_1$-$C_4$alkyl, $C_3$-$C_7$cycloalkyl, $C_1$-$C_4$alkoxy, mono- and di-($C_1$-$C_4$alkyDamino, $C_2$-$C_6$alkoxycarbonyl, $C_1$-$C_2$haloalkyl (specifically fluoroalkyl), or $C_1$-$C_2$haloalkoxy (specifically fluoroalkoxy).

In another embodiment, the inhibitor includes compounds and pharmaceutically acceptable salts of Formula Ia and Ib:

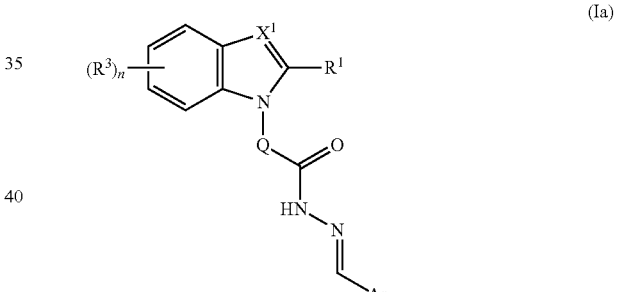

(Ia)

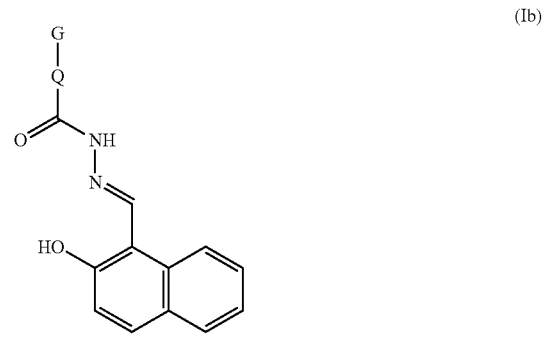

(Ib)

wherein G, Q, $R^1$, $X^1$, $R^3$, n, Q, and Ar are as previously defined. In one embodiment, Ar is substituted naphthalene, specifically substituted with a hydroxy group or a methoxy group, or Ar is a substituted phenyl specifically substituted with a hydroxy group. In one embodiment, $R^1$ is H, $CF_3$ or $CH_3$. In one embodiment, Q is $C_2$alkyl.

In specific embodiments, the cell division inhibitor is compound 1 or its trifluoro analog, compound 6:

Compound 1

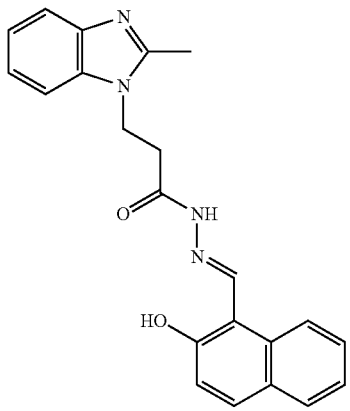

Compound 6

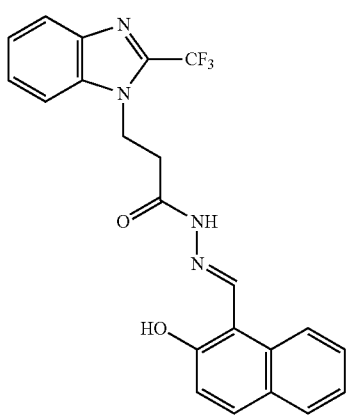

Additional analogs of compound 1 are compounds 7-9:

Compound 7

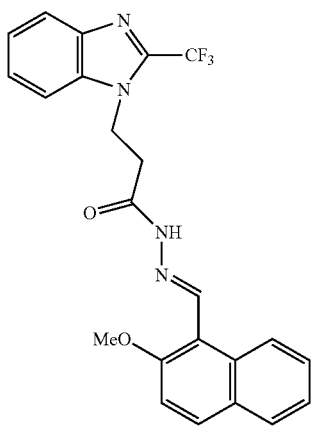

Compound 8

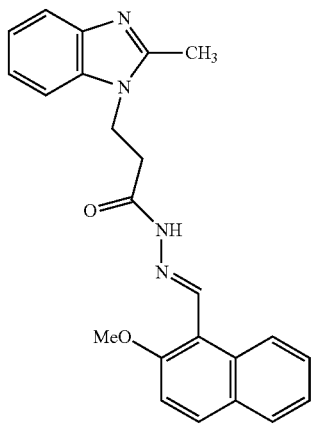

Compound 9

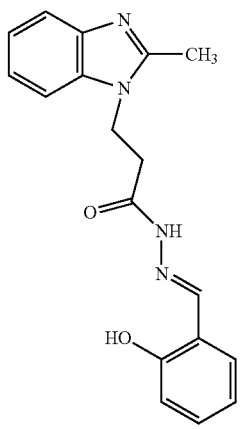

In certain situations, the compounds of Formulae I and Ia may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with double bonds may occur in Z- and E-forms, with all isomeric forms of the compounds being included in the present disclosure. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The term "substituted", as used herein, means that any one or more hydrogens on the designated atom or group is replaced with a selection from the indicated group, provided that the designated atom's normal valence is not exceeded. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —COOH is attached through the carbon atom.

As used herein, "alkyl" is intended to include both branched and straight-chain saturated aliphatic hydrocarbon groups, having the specified number of carbon atoms. Thus, the term $C_1$- $C_6$alkyl as used herein includes alkyl groups having from 1 to about 6 carbon atoms. When $C_0$-$C_n$ alkyl is used herein in conjunction with another group, for example, phenyl$C_0$-$C_4$alkyl, the indicated group, in this case phenyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl.

"Alkenyl" as used herein, indicates hydrocarbon chains of either a straight or branched configuration comprising one or more unsaturated carbon-carbon bonds, which may occur in any stable point along the chain, such as ethenyl and propenyl.

"Alkynyl" as used herein, indicates hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy,2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

The term "alkoxycarbonyl" indicates an alkoxy group, as defined above, having the indicated number of carbon atoms, attached through a keto linkage. The carbon of the keto linker is not included in the numbering, thus a $C_2$alkoxycarbonyl has the formula $CH_3CH_2O(C=O)$—.

The term "alkylcarboxamide" indicates an alkyl group, as defined above, having the indicated number of carbon atoms, attached through a carboxamide linkage, i.e., a —$CONH_2$ linkage, where one or both of the amino hydrogens is replaced by an alkyl group. Alkylcarboxamide groups may be mono- or di-alkylcarboxamide groups, such an ethylcarboxamide or dimethylcarboxamide.

As used herein, the term "mono- or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, the term "aryl" indicates aromatic groups containing only carbon in the aromatic ring or rings. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl", aryl and alkyl are as defined above, and the point of attachment is on the alkyl group. This term encompasses, but is not limited to, benzyl, phenylethyl, and piperonyl. Likewise, in the term (aryl)carbhydryl, aryl and carbhydryl are as defined above and the point of attachment is on the carbhydryl group, for example a phenylpropen-1-yl group.

"Carbhydryl" as used herein, includes both branched and straight-chain hydrocarbon groups, which are saturated or unsaturated, having the specified number of carbon atoms.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norbornane or adamantane.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trffluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline. In the term "heteroarylalkyl," heteroaryl and alkyl are as defined above, and the point of attachment is on the alkyl group. This term encompasses, but is not limited to, pyridylmethyl, thiophenylmethyl, and pyrrolyl(1-ethyl).

The term "heterocycloalkyl" is used to indicate saturated cyclic groups containing from 1 to about 3 heteroatoms chosen from N, O, and S, with remaining ring atoms being carbon. Heterocycloalkyl groups have from 3 to about 8 ring atoms, and more typically have from 5 to 7 ring atoms. A $C_2$-$C_7$heterocycloalkyl group contains from 2 to about 7 carbon ring atoms and at least one ring atom chosen from N, O, and S. Examples of heterocycloalkyl groups include morpholinyl, piperazinyl, piperidinyl, and pyrrolidinyl groups.

"Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

In one aspect, provided herein are methods of treating a subject in need of treatment for a bacterial infection, comprising administering to the individual a cell division inhibitor (also referred to herein as an antimicrobial compound) as described herein. The bacteria causing the infection can be Gram-negative or Gram-positive bacteria, specifically Gram-negative bacteria. Gram-negative bacteria include *Escherchia coli, Caulobacter crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Shigella boydii, Vibrio cholera, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Morganella morganii, Edwardsiella tarda, Acinetobacter baumannii* and *Haemophilus Influenzae*. In another embodiment, the bacteria are Gram-positive bacteria. Gram-positive bacteria include species of *Bacillus, Listeria, Staphylococcus, Streptococcus, Enterococcus, Enterobacter, Corynebacterium, Propionibacterium* and *Clostridium*. Specific Gram-positive bacteria include *Staphylococcus aureus, Staphylococcus epidermidis, Enterococcus Faecium*, and *Bacillus subtilis*. In a specific embodiment, the bacteria are one or more drug resistant bacteria.

In another aspect, a method of inhibiting bacterial growth comprises contacting the bacteria with an antimicrobial compound as described herein. Methods of inhibiting bacteria include methods useful for treatment of a subject (human or veterinary) and also include methods useful for inhibiting bacteria outside of a subject, such as use for sterilization and disinfection.

The antimicrobial compounds and compositions may be administered prophylactically, chronically, or acutely. For example, such compounds may be administered prophylactically to patients known to be prone to bacterial infections, or who are known to have been exposed to potentially infectious agents. The compounds may also be administered prophylactically to patients suffering other conditions, such as AIDS or other immune-system-suppressing conditions, that render them susceptible to opportunistic infections. In addition to the prevention of such infections, chronic administration of the antimicrobial compounds will typically be indicated in treating refractory conditions, such as persistent infection by multiple drug-resistant strains of bacteria. Acute administration of the antimicrobial compounds is indicated to treat, for example, those subjects presenting with classical indications of bacterial infection.

As used herein, "contacting" means that a compound is provided such that it is capable of making physical contact with another element, such as a microorganism, a microbial culture or a substrate. In another embodiment, the term "contacting" means that the compound is introduced into a subject receiving treatment, and the compound is allowed to come in contact in vivo. Thus, contacting can include administration of a compound, that is, introducing the compound into the body, such as into the systemic circulation. Administration routes include but are not limited to, rectal, oral; buccal, sublingual, pulmonary, transdermal, transmucosal, as well as subcutaneous, intraperitoneal, intravenous, and intramuscular injection.

Since the antimicrobial compounds are antibacterially active and inhibit bacterial growth, they are also of use in treating bacterial contamination of a substrate, such as hospital instruments or work surfaces. In order to treat a contaminated substrate, the compounds may be applied to the site of such contamination in an amount sufficient to inhibit bacterial growth.

In certain embodiments, the compounds are administered to a patient or subject. A "patient" or "subject", used equivalently herein, means mammals and non-mammals. "Mammals" means a member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The phrase "effective amount," as used herein, means an amount of an agent which is sufficient enough to significantly and positively modify symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The phrase "inhibitory amount", as used herein, means an amount of an agent (a compound or composition) which is sufficient to reduce the level or activity of bacterial infection to a statistically significant lesser value as compared to when the agent is not present.

The amount of compound effective for any indicated condition will, of course, vary with the individual subject being treated and is ultimately at the discretion of the medical or veterinary practitioner. The factors to be considered include the condition being treated, the route of administration, the nature of the formulation, the subject's body weight, surface area, age and general condition, and the particular compound to be administered. In general, a suitable effective dose is in the range of about 0.1 to about 500 mg/kg body weight per day, preferably in the range of about 5 to about 350 mg/kg per day. The total daily dose may be given as a single dose, multiple doses, e. g., two to six times per day, or by intravenous infusion for a selected duration. Dosages above or below the range cited above may be administered to the individual patient if desired and necessary.

As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art. Topical administration includes transdermal formulations such as patches.

For topical application to the eye, the inhibitor may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

The antimicrobial compounds may also be administered in combination with an additional active agent, such as, for example, an inhibitor of bacterial efflux. Efflux pumps are proteins that unidirectionally remove antibiotics from cytoplasmic compartments, and are considered to be a mechanism of antibacterial resistance. Bacterial efflux inhibitors include chalcone compounds as disclosed in WO 11/075136, the polybasic compounds disclosed in WO 10/054102, the quaternary alkyl ammonium functional compounds disclosed in WO 08/141012, the compounds disclosed in WO 05/007162, the substituted polyamines of WO 04/062674, which are incorporated herein by reference in their entirety.

In another embodiment, the antimicrobial compounds of formula 1 can be administered with a second antibiotic. Exemplary second antibiotics include, for example, glycopeptides (e.g, vancomycin or teicoplanin); penicillins, such as amdinocillin, ampicillin, amoxicillin, azlocillin, bacampicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin; cephalosporins, such as cefadroxil, cefazolin, cephalexin, cephalothin, cephapirin, cephradine, cefaclor, cefamandole, cefonicid, ceforanide, cefoxitin, and cefuroxime, cefoperazone, cefotaxime, cefotetan, ceftazidime, ceftizoxime, ceftriaxone, and moxalactam; carbapenems such as imipenem; monobactams such as aztreonam; tetracyclines such as demeclocycline, tigilcycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, and polymyxin B, and erythromycins and lincomycins and also sulfonamides such as sulfacytine, sulfadiazine, sulfisoxazole, sulfamethoxazole, sulfamethizole, and sulfapyridine; trimethoprim, quinolones, novobiocin, pyrimethamine, and rifampin; and combinations thereof.

The invention is further illustrated by the following non-limiting examples.

EXAMPLES

Example 1

Selection of Cell Division Inhibitors

In vitro ATPase screen with purified recombinant MipZ: The assays used for screening compounds were a coupling assay and a fluorescence polarization assay of MipZ ATPase activity. Recombinant MipZ for the in vitro screen was purified as described in Thanbichler and Shapiro (*Cell*, 2006). Two ATPase assays were used to screen three small molecule libraries (a total of 43,400 compounds) at the University of Wisconsin Carbone Cancer Center. One assay utilized pyruvate kinase and lactic dehydrogenase as coupling enzymes and phosphoenolpyruvate and NADH, respectively, as their substrates. A solution of coupling enzymes, their substrates, Triton X, and MipZ was aliquoted (22.3 µL per well) into 384-well black plates using a Biomek FX liquid handler (Beckman Coulter). Plates were briefly centrifuged to pull liquids to the bottom of the wells. Pin tools were used to deliver 0.2 µL of a unique small molecule to each well from a stock solution (10 mM in DMSO) from the chemical libraries. The first two columns of each plate were reserved for controls and did not receive compounds from the libraries. Using Biotek Fill, ATP hydrolysis was initiated by adding a solution of ATP to each well, with the exception of those in the first column of each plate. The final concentrations of the assay components were as follows: 0.01% Triton X, 1 mM phosphoenolpyruvate, 0.3 mM NADH, 3 U/mL pyruvate kinase, 3 U/mL lactic dehydrogenase, 7.5 µM MipZ, and 1 mM ATP in a buffered solution of 50 mM Tris-HCl, 50 mM KCl, and 10 mM $MgCl_2$. Plates were gently vortexed to mix the solution and incubated for three hours at 30° C. After incubation, the fluorescence emission from NADH was measured using a Tecan Safire II™ ($\lambda_{ex}$=340/35 nm; $\lambda_{em}$=460/10 nm). The fluorescence intensity in the control wells was used to calculate the Z-factor; the minimum Z-factor for all plates was 0.7. The coupling enzyme assay was used to screen compounds from the Maybridge and Life Chemicals libraries. Compounds that inhibited ≥60% of ATP hydrolysis compared with the positive control were identified as hits, and they were screened using a secondary assay to eliminate compounds that target coupling enzymes. The secondary assay consisted of the same reaction components as the primary assay with two exceptions: (1) MipZ was omitted, and (2) ATP was replaced with ADP. The compounds that did not inhibit coupling enzymes were then checked for intrinsic fluorescence at the specified wavelengths used for NADH and retested for their activity against MipZ in vitro.

In addition to the coupling enzyme assay, a fluorescence polarization (FP) assay was used to monitor the ATPase activity of MipZ in vitro. (FIG. 2) Reaction conditions and component concentrations were same as in the coupling enzyme assay unless otherwise noted. The FP assay utilized anti-ADP antibodies and Alexa 633-labeled ADP. The Transcreener® $ADP^2$ FP assay kit was purchased from Bell Brook Labs. A solution of MipZ was aliquoted into plates (10 µL per well), and the reaction was initiated by the addition of ATP (1 µL of 5 mM stock solution per well). After three hours, 10 µL of ADP detection mix (541 µg/mL of antibody) was added to each well, and the plates were further incubated for 1 hr at RT. The wavelengths used for FP measurements were 635 nm for excitation and 670/20 nm for emission. The Z-factor for the FP assay was ≥0.7. The FP assay was used to screen compounds from the Life Chemicals library and the Spectrum Collection. Hits from the FP assay were checked for intrinsic fluorescence at the specified wavelengths used for the Alexa 633 probe and tested for any potential inhibition of the anti-ADP antibody by repeating the assay in the absence of MipZ.

Example 2

Screening of Hits for Antibacterial Activity

In vivo screen with a *Caulobacter crescentus* strain that expresses MipZ-YFP: Hits from the in vitro screens were tested for their activity in vivo. A *C. crescentus* strain (MT97) that expresses mipZ-yfp from the native mipZ promoter was used. An overnight culture of MT97 was diluted to an $OD_{600}$ of ~0.1, and the diluted culture was further grown for at least an hour prior to treatment with the compound. Compounds were mixed with a solution of 1% agarose in M2G medium to achieve a final concentration of 20 µM. Cells were inoculated onto the surface of the compound-containing agarose pad (1 µL inoculum per pad), and we observed the cell morphology and localization of MipZ-YFP for a period of 24 hrs. In the time between microscopic observations, the inoculated pads were kept at 30° C. to promote growth.

Figure 3:
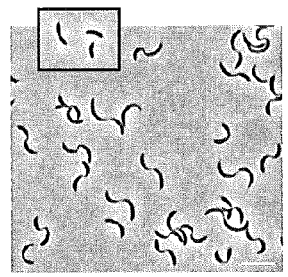
FIG. 3 shows that compound 1 inhibits septation during reproduction in *C. crescentus* and *Escherichia coli*.
Figure 3:
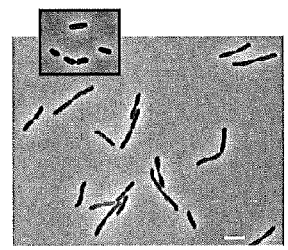

As can be seen in FIG. 3, compound 1 inhibits septation during reproduction in *C. crescentus*. The phenotype looks similar to overexpression of FtsZ, suggesting that compound 1 affects cell division.

Example 3

Determination of the MIC of Compound 1

Determination of the minimum inhibitory concentration (MIC): The MIC of the small molecule hits was determined using a macrodilution method. All cultures were grown in M8 medium at 37° C., except for *C. crescentus* (strain CB15N) which was cultured in PYE media at 30° C. *C. crescentus* and *E. coli* cultures were incubated while shaking at 200 rpm. Pathogenic clinical strains were grown in static conditions. All cultures were grown for 17 hrs.

The MIC of compound 1 for *C. crescentus* was 5 µM, while for *E. coli* ΔtolC it was 13.5 µM, suggesting activity against Gram-negative bacteria. *E. coli* ΔtolC is a knockout of a component of the drug efflux pump, which results in a cell without an effective pump, and was used in place of an efflux pump inhibitor in these experiments. The MIC of P190723 for *E. coli* reported in the literature is >180 µM. The MICs of compound 1 against pathogenic strains are 0.4 µM for *Vibrio cholerae*, 50 µM for *Shigella boydii*, and 25 µM for *Acinetobacter baumannii*.

Example 4

Use of Microscopy to Visualize the Effects of Compound 1 on Cell Division

Optical microscopy and image analysis: A Nikon Eclipse TE2000E inverted microscope with a Perfect Focus system and an encoded z-stage for phase contrast and epifluorescence microscopy was used. To observe the effect of Compound 1 on cell division, freshly grown cells from an overnight culture were treated with the compound. Small aliquots (1-2 µL) of the cells dosed with Compound 1 were mounted on 1% agarose pads for microscopy. To visualize FtsZ localization, MT196 cells (*C. crescentus* CB15N $P_{vanA}$-ftsZ-yfp) were induced with vanilate (0.5 mM) for 1 hr prior to imaging. PSICIC, a MATLAB-based script, was used to measure cell lengths (n≥100) for the following strains of *C. crescentus*: CB15N, CB15N pMT182 ($P_{xylX}$-mipZ, $Cm^R$), and CB15N ΔzapA. The CB15N pMT182 strain was treated with 0.2% xylose to induce overexpression of MipZ. For cells that could not be accurately detected by PSICIC, the cell length was manually traced in MetaMorph or ImageJ and the pixel traces were converted to microns. GraphPad InStat was used for statistical analysis of cell length distributions.

Figure 4:
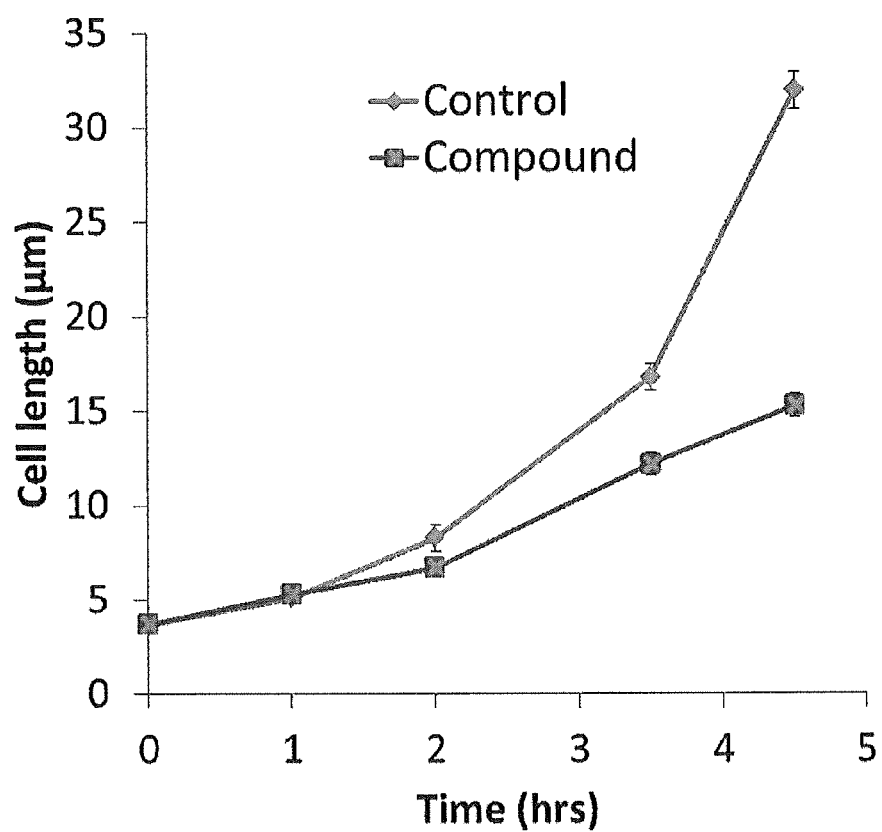
FIG. 4 shows that compound 1 rescues cell elongation caused by MipZ overexpression.

As shown in FIG. 4, compound 1 rescues cell elongation caused by MipZ overexpression. MipZ overexpression inhibits FtsZ assembly at the division plate and causes filamentation. Compound 1 rescues this phenotype suggesting that compound 1 stabilizes FtsZ filaments.

Figure 5:
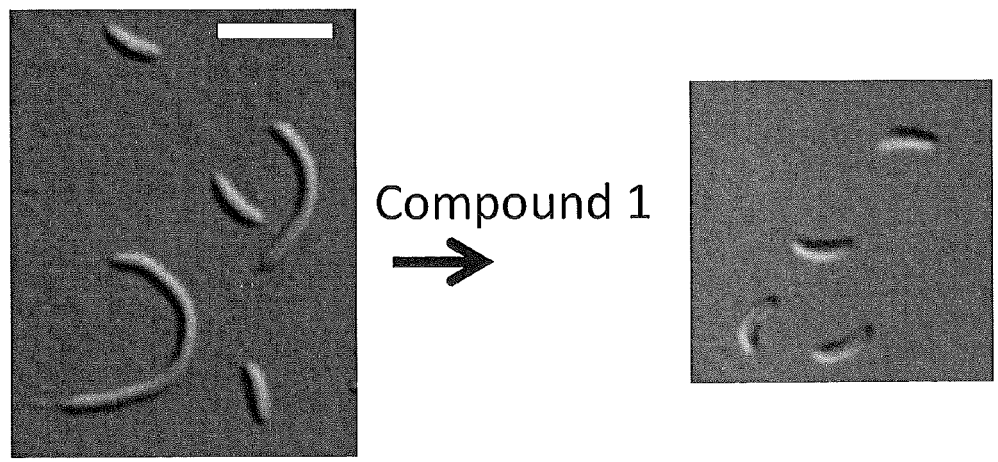
FIGS. 5 and 6 show that compound 1 rescues division defects in a *C. Crescentus* ΔzapA strain.
Figure 6:
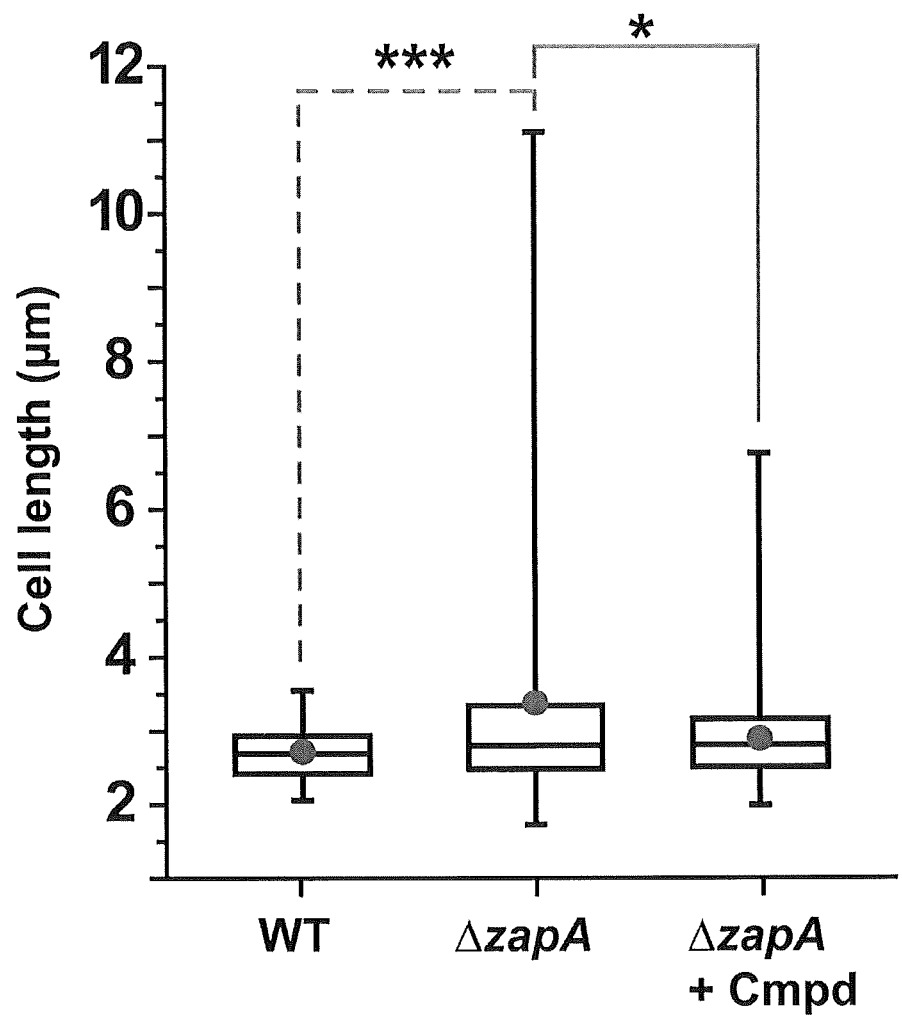

As shown in FIGS. 5 and 6, compound 1 also rescues division defects in a *C. crescentus* ΔzapA strain. ZapA stabilizes FtsZ in vivo and induces FtsZ bundling in vitro. Deletion of ZapA leads to a heterogeneity in cell length. Addition of compound 1 to a ΔzapA strain restores cell lengths to near normal lengths.

Example 5

Viability of *C. crescentus* after Exposure to Antibiotics

Figure 7:
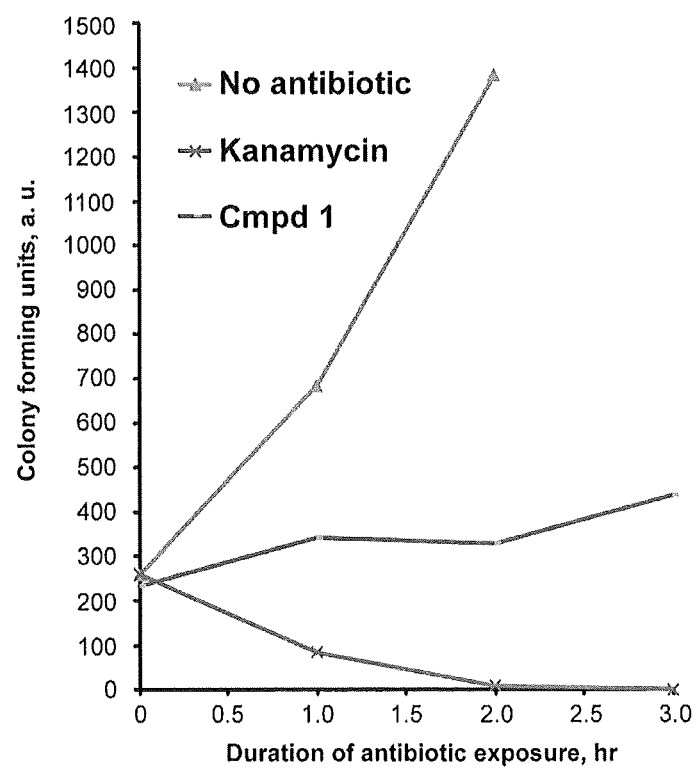
FIG. 7 shows viability of *C. crescentus* after exposure to kanamycin and compound 1.

Viable *C. crescentus* cells were counted after treatment with antibiotics to determine the toxicity effect of compound 1 on bacteria. Kanamycin was used as a control since it is a known bacteriocidal agent. An overnight culture of CB15N in PYE medium was diluted to an optical density of 0.1 ($\lambda$=600 nm) and incubated further for 1.5 hrs. After the incubation, the culture was aliquoted into 15 mL conical tubes (1 mL of culture per aliquot) and treated with antibiotics. The final concentration of the antibiotics was twice its minimum inhibitory concentration. Upon addition of antibiotics, the culture tubes were wrapped with aluminum foil and shaken at 250 rpm at 30° C. At every 30 min, 100 µL was withdrawn from each aliquot and serially diluted five times in M2G medium. 100 µL of the fifth dilution was spread on PYE plates, the plates were incubated for two days at 30° C., and the number of colonies formed on the plates was counted. As shown in FIG. 7, the number of colonies increased over time due to cell growth and division when no antibiotics were added to the culture. On the other hand, a bacteriocidal antibiotic, kanamycin, decreased the colony forming units since it induces cell death. Treating with compound 1 did not significantly alter the colony forming units over time, indicating that it acts as a bacteriostatic agent to limit reproduction of bacteria.

Example 6

Compound 1 Perturbs the localization of FtsB, FtsL, FtsK and FtsI in *C. crescentus* cells Strains of *C. crescentus* that express fluorescently-tagged Fts proteins (FtsB, FtsL, FtsK, and FtsI) were cultured overnight. The overnight cultures were diluted 10-fold and incubated for an hour at 30° C. prior to compound treatment. Cells were induced with xylose (0.3%) to trigger the expression of fluorescently-tagged Fts proteins. After inducing with xylose for 45 min, cells were mounted on agarose pads and imaged as described in Example 4.

Figure 8:
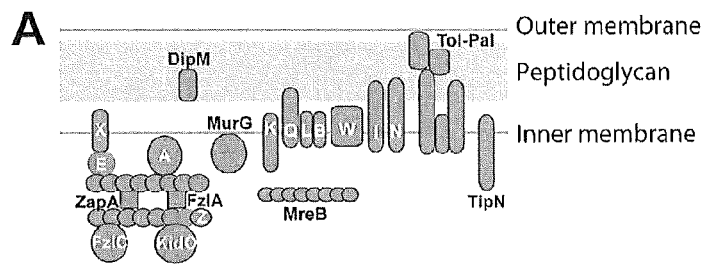
FIG. 8 shows that compound 1 perturbs the localization of several Fts proteins, including FtsB, FtsL, FtsI, and FtsK, in *C. crescentus*.
Figure 8:
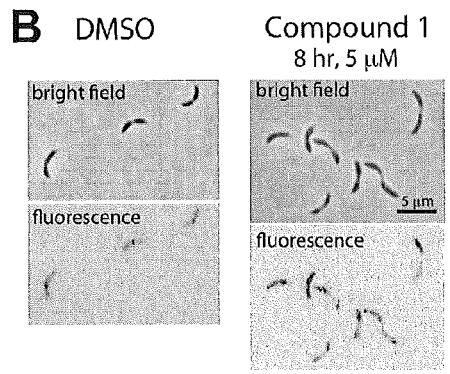
Figure 8:
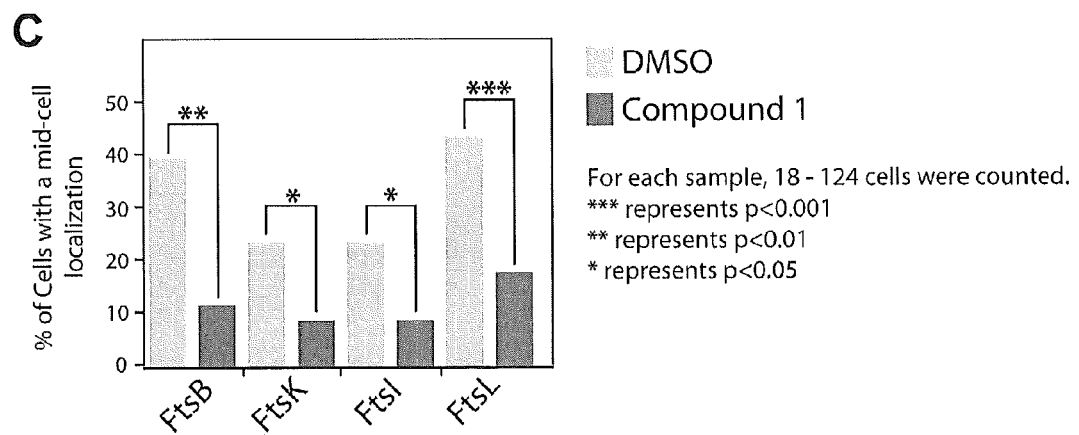

To analyze changes in the localization of Fts proteins, cells in the late division stage were selected for image analysis. At this stage of the cell cycle, cells have a visible constriction at the midcell, and the Fts proteins localize to the constriction site. FIG. 8A (taken from Goley et al., 2011, *Molecular Microbiology*) shows a schematic of various division proteins that are recruited to the septum following the localization of FtsZ. Within the population of cells selected for a visible constriction, cells that have a single fluorescence focus of Fts proteins were counted. FIG. 8B shows representative images for cells expressing Venus-FtsI. These cells have clear constrictions at the midcell as shown in brightfield images. In the fluorescence channel, the signal from Venus-FtsI is localized at the septum in the DMSO sample. In contrast, the fluorescence signal is more diffuse throughout the cell body in the sample treated with compound 1. We calculated the percentage of cells with a fluorescence signal at the midcell, and found that the treatment with compound 1 decreased the population of cells with a midcell localization of Fts proteins (FIG. 8C). The observed decrease in Fts protein localization in the presence of compound 1 was statistically significant when compared to the DMSO solvent control samples. This perturbation of division protein localization suggests that compound 1 inhibits the proper assembly and maturation of the bacterial division machinery.

Example 7

Figure 9:
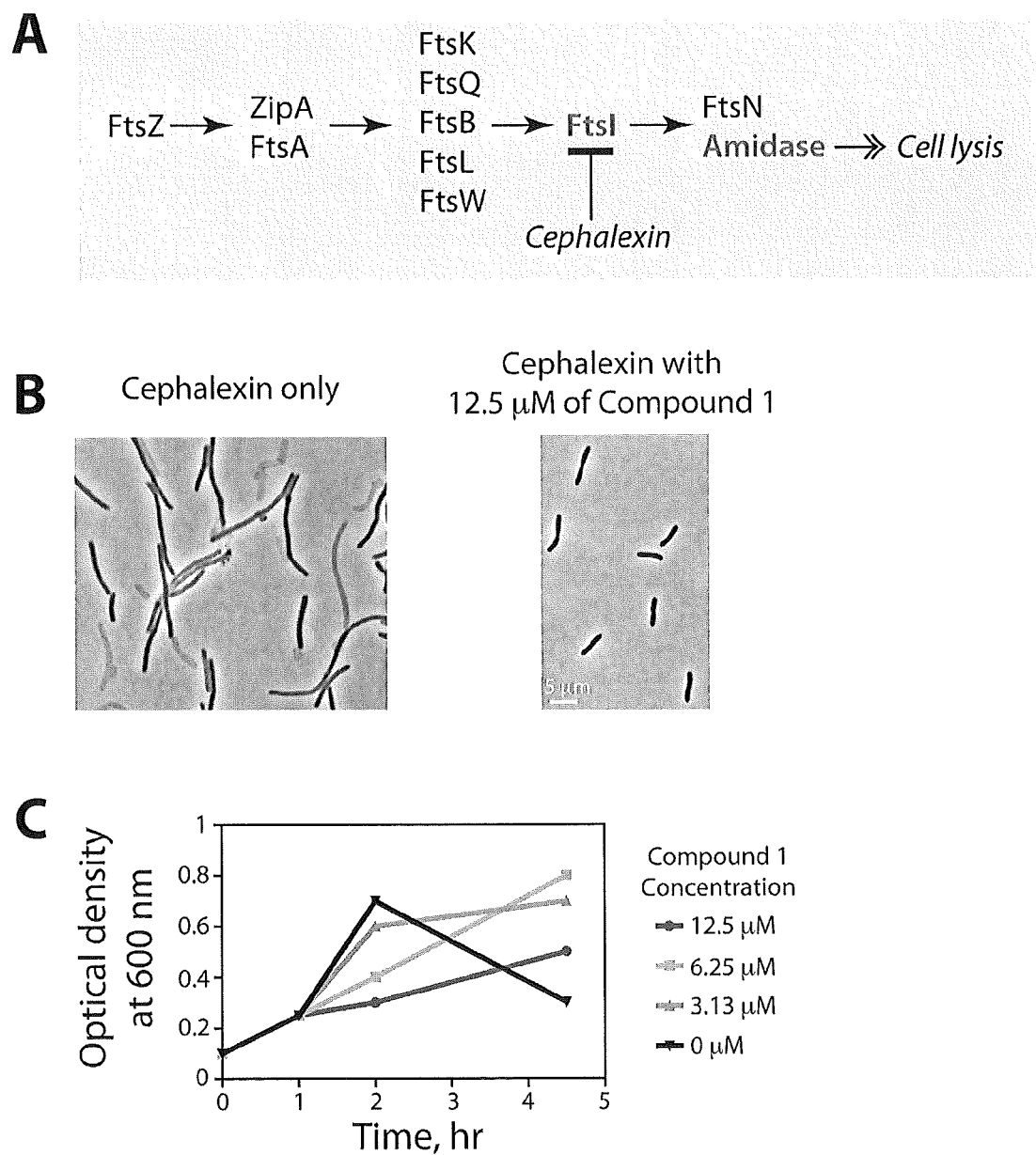
FIG. 9 shows that compound 1 perturbs the assembly of division proteins in *E. coli* cells.

Co-Treatment with Compound 1 Decreases Cell Lysis and Filamentation Induced by Cephalexin Cephalexin belongs to a family of β-lactam antibiotics that target the synthesis of peptidoglycan cell wall. This compound binds to the active site of FtsI to inhibit crosslinking of peptidoglycan at the septum. When cephalexin is added to *E. coli* cells, some cells undergo lysis while others elongate. A proposed mechanism for the cephalexin-induced cell lysis is shown in FIG. 9A (adopted from Chung et al., 2009, *PNAS*). This model suggests that the inhibition of FtsI activity by cephalexin does not affect the enzyme's ability to localize to the septum and recruit downstream division proteins, including FtsN and amidases. Amidases readily cut the peptidoglycan at the septum to create holes for inserting new materials. When cephalexin is present, however, the holes created by amidases cannot be repaired by FtsI. This inability to repair gaps in the peptidoglycan leads to cell lysis in cephalexin-treated samples. We utilized this mechanism of cephalexin-induced cell lysis to test whether the assembly of divisome is perturbed in the presence of compound 1. To this end, we used the *E. coli* ΔtolC construct to measure the amount of cell lysis in the presence of compound 1 and cephalexin. The *E. coli* cells were grown overnight to stationary phase, and the overnight culture was diluted to an optical density of 0.1 (measured at $\lambda_{600}$). The dilution was grown for another 1 hour at 37° C. to reach an optical density of 0.25. At this point, 10 µg/mL of cephalexin was added to the culture, and a 2-fold serial dilution was made to test a range of compound 1 concentrations (0 to 12.5 µM). After the addition of compounds, we measured the optical density of cultures. As shown in FIG. 9B, cells became filamented and underwent lysis in the presence of cephalexin. The optical density increases due to cell filamentation (between 1 to 2 hr time points for the sample without compound 1 in FIG. 9C) and eventually decreases as cells start lysis. Compared to this pattern in the optical density of the cephalexin-only control, we observed that cells co-treated with cephalexin and compound 1 elongated slowly and did not undergo cell lysis, as indicated by the steady increase in their optical density (FIG. 9C). This decreased sensitivity to cephalexin in the presence of compound 1 suggests that some late division proteins (e.g. amidases) either could not function properly at the division site, or did not localize to the septum. In summary, the data presented here collectively indicate that assembly and maturation of the bacterial divisome have been perturbed by compound 1.

Example 8

Inhibition of Cell Division by Compound 1 is Reversible

Figure 10:
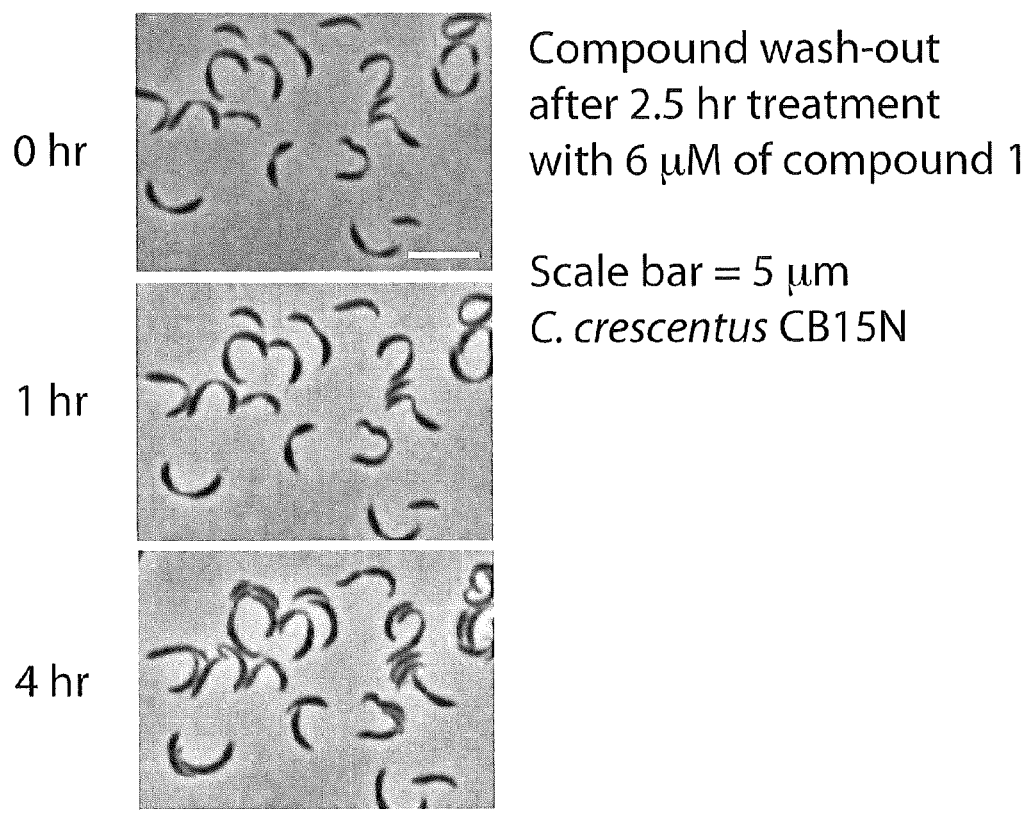
FIG. 10 shows that the inhibitory effect of compound 1 on cell division is reversible.

To test whether the inhibitory effect of compound 1 is reversible, the compound was washed out of pre-treated cells and their growth and division monitored using microscopy. A culture of *C. crescentus* CB15N cells was pre-incubated with 6 μM compound 1 for 2.5 hours at 30° C. A small aliquot of this culture was applied to an agarose pad (2% w/v agarose in PYE media), and the cells were imaged over time while incubating them on the microscope stage at 30° C. As shown in FIG. 10, cells were able to grow and resume division as the small molecule diffused out. This relief of inhibition on cell division indicates that the inhibitory effect of compound 1 is reversible.

Example 9

Preparation of Compound 1

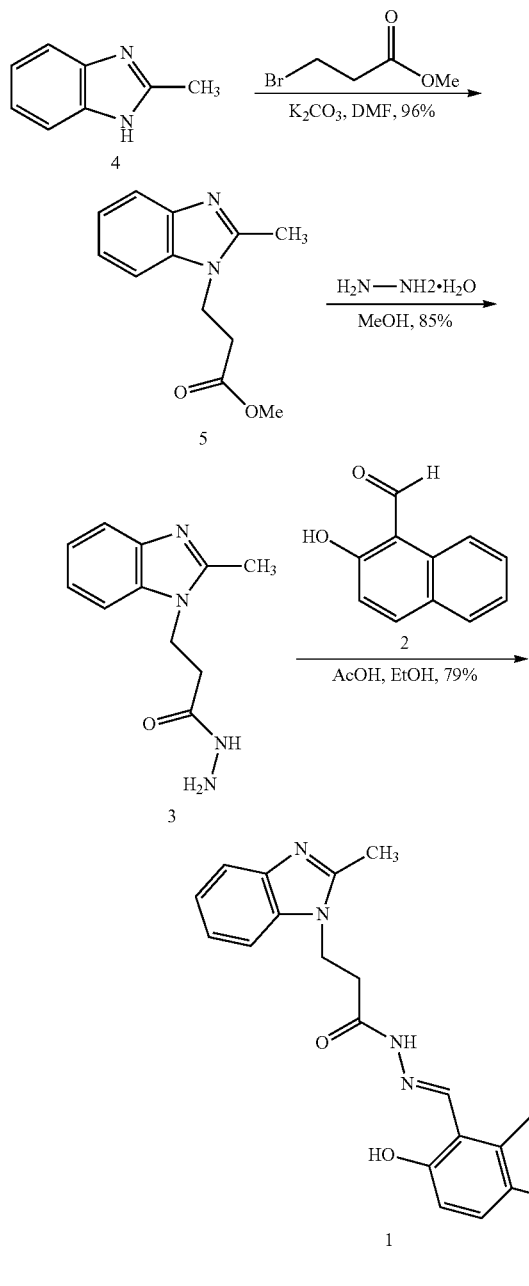

Compound 1 is prepared by the condensation of 2-hydroxy-1-naphthaldehyde (2) and 3-(2-methyl-1H-benzimidazol-1-yl)propanohydrazide (3). The intermediate 3 was prepared through the hydrazinolysis of methyl ester 5, which in turn was prepared by the reaction of 2-methyl-1H-benzimidazole (4) with methyl 3-bromopropionate in the presence of anhydrous potassium carbonate as a base.

Example 10

Preparation of Compound 6

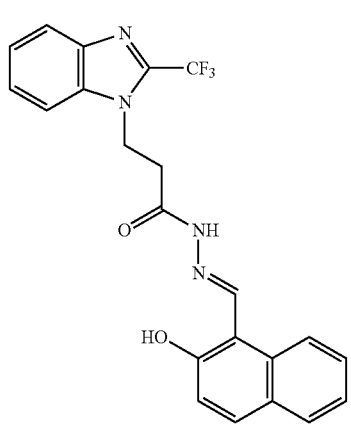

Compound 6 is prepared similarly to Compound 1 in Example 9 using 2-(trifluoromethyl)-1H-benzo[d]imidazole as the starting material.

Example 11

Preparation of Compound 7

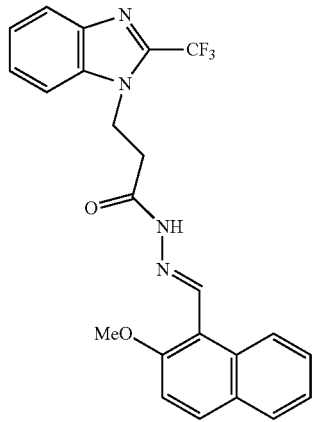

Compound 7 is prepared similarly to Compound 1 in Example 9 using 2-(trifluoromethyl)-1H-benzo[d]imidazole and 2-methoxy-1-naphthaldehyde as the starting material.

Example 12

Preparation of Compound 8

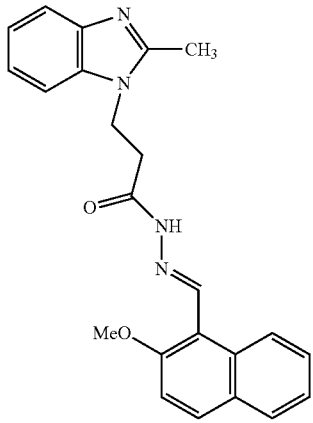

Compound 8 is prepared similarly to Compound 1 in Example 9 using 2-methoxy-1-naphthaldehyde as the starting material.

Example 13

Preparation of Compound 9

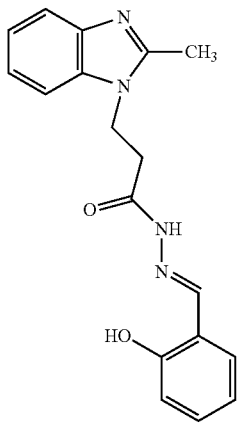

Compound 9 is prepared similarly to Compound 1 in Example 9 using 2-hydroxy-1-benzylaldehyde as the starting material.

Minimum inhibitory concentration for compounds 1, 6, 7, 8, and 9, determined as in Example 3 using the *C. crescentus* CB15N strain.

| Compound | Minimum Inhibitory Concentration, MIC (μM) |
|---|---|
| 1 | 5 |
| 6 | 7.5 |
| 7 | >20 |
| 8 | >20 |
| 9 | 15 |

Disclosed herein is a novel class of antimicrobial, specifically antibacterial compounds, that inhibit cell division in bacteria. Compound 1 and it analogs as described herein are expected to have potent antibacterial activity, particularly against Gram-negative bacteria. Because of the growing problem of resistance to known antibiotics such as vancomycin, the development of novel antibiotics is very important to the treatment of bacterial infections. Compound 1 is bacteriostatic, that is, it inhibits the reproduction of bacterial cells but does not kill the microbes. This characteristic reduces the selective pressure on the microbial population for acquisition of resistant mutations; thus the probability of developing resistance is smaller for the bacteriostatic compound 1.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of treating a subject in need of treatment for a bacterial infection, comprising
administering to the subject an effective amount of a cell division inhibitor of Formula Ib, or a pharmaceutically acceptable salt thereof:

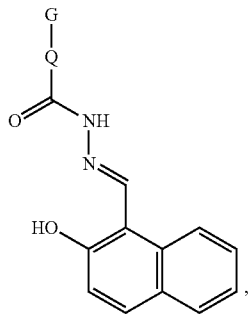

Formula Ib wherein G is

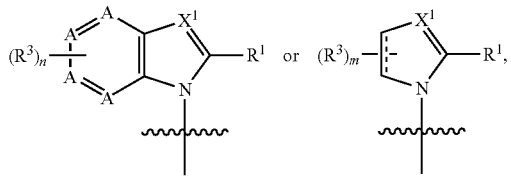

wherein each instance of A is independently CH or N provided that the total number of N is 0 or 1;
$R^1$ is hydrogen, hydroxy, amino, halogen, cyano, $C_1$-$C_6$alkyl, $C_1$-$C_6$alkoxy, $C_1$-$C_6$haloalkyl, $C_1$-$C_6$haloalkoxy, aryl, or (aryl)alkyl;
$X^1$ is N, $CR^2$, O, or S;
$R^2$ is hydrogen, $C_1$-$C_6$alkyl, $C_1$-$C_6$alkoxy, $C_1$-$C_6$haloalkyl, $C_1$-$C_6$haloalkoxy, aryl, or (aryl)alkyl;
each instance of $R^3$ independently is hydroxy, sulfate, nitro, amino, halogen, cyano, $C_1$-$C_4$alkyl, $C_1$-$C_4$alkoxy, $C_3$-$C_7$cycloalkyl, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, phenyl, pyridyl, heterocycloalkyl, alkylcarboxamide, $C_2$-$C_4$alkenyl, or $C_2$-$C_4$alkynyl;
n is 0, 1, or 2;
m is 0 or 1;
Q is a bond or a $C_1$-$C_6$ hydrocarbon linking group, wherein the linking group is substituted by 0, 1, 2, or 3 substituents independently chosen from hydroxy, sulfate, nitro, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, or oxo;
wherein the 2-hydroxy-1-naphthalenyl group is substituted with 0, 1, or 2 hydroxy substituents.

2. The method of claim 1, wherein the individual is infected with a Gram-negative bacteria or a Gram-positive bacteria.

3. The method of claim 2, wherein the individual is infected with a Gram-negative bacteria selected from *Escherchia coli, Caulobacter crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Salmonella typhimuriwn, Neisseria meningitidis, Serratia marcescens, Shigella sonnei, Shigella boydii, Vibrio cholera, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Morganella morganii, Edwardsiella tarda, Acinetobacter baumannii* and *Haemophilus influenzae*.

4. The method of claim 1, wherein administering is prophylactic, acute or chronic.

5. The method of claim 1, wherein the subject is a mammal.

6. The method of claim 5, further comprising administering a bacterial efflux inhibitor.

7. A method of inhibiting bacterial growth, comprising contacting the bacteria with a cell division inhibitor of Formula Ib or a pharmaceutically acceptable salt thereof:

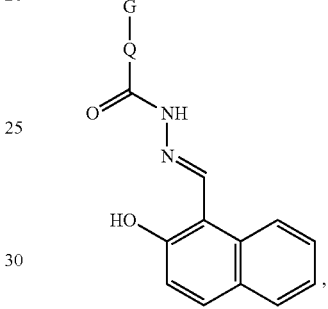

Formula Ib wherein G is

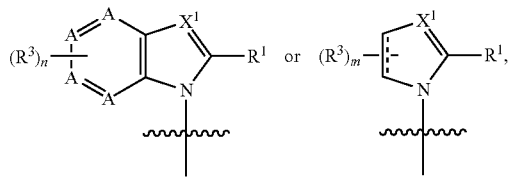

wherein each instance of A is independently CH or N provided that the total number of N is 0 or 1;
$R^1$ is hydrogen, hydroxy, amino, halogen, cyano, $C_1$-$C_6$alkyl, $C_1$-$C_6$alkoxy, $C_1$-$C_6$haloalkyl, $C_1$-$C_6$haloalkoxy, aryl, or (aryl)alkyl;
$X^1$ is N, $CR^2$, O, or S;
$R^2$ is hydrogen, $C_1$-$C_6$alkyl, $C_1$-$C_6$alkoxy, $C_1$-$C_6$haloalkyl, $C_1$-$C_6$haloalkoxy, aryl, or (aryl)alkyl;
each instance of $R^3$ independently is hydroxy, sulfate, nitro, amino, halogen, cyano, $C_1$-$C_4$alkyl, $C_1$-$C_4$alkoxy, $C_3$-$C_7$cycloalkyl, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, phenyl, pyridyl, heterocycloalkyl, alkylcarboxamide, $C_2$-$C_4$alkenyl, or $C_2$-$C_4$alkynyl;
n is 0, 1, or 2;
m is 0 or 1;
Q is a bond or a $C_1$-$C_6$ hydrocarbon linking group, wherein the linking group is substituted by 0, 1, 2, or 3 substituents independently chosen from hydroxy, sulfate, nitro, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_2$-$C_6$alkanoyl, $C_1$-$C_2$haloalkyl, $C_1$-$C_2$haloalkoxy, or oxo;

wherein the 2-hydroxy-1-naphthalenyl group is substituted with 0, 1, or 2 hydroxy substituents.

8. The method of claim 7, wherein contacting comprises application of the compound to a contaminated substrate.

9. The method of claim 7, wherein the bacteria is a Gram-negative bacteria or a Gram-positive bacteria.

10. The method of claim 9, wherein the bacteria is a Gram-negative bacteria selected from *Escherchia coli, Caulobacte crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Shigella boydii, Vibrio cholera, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Morganella morganii, Edwardsiella tarda, Acinetobacter baumannii,* and *Haemophilus influenza.*

11. The method of claim 1, wherein Q is a $C_1$-$C_3$ hydrocarbon linking group substituted by 0, 1, 2, or 3 substituents independently chosen from hydroxy, amino, halogen, $C_1$-$C_2$alkyl, $C_3$-$C_5$cycloalkyl, $C_1$-$C_2$alkoxy, mono- and di-($C_1$-$C_2$alkyl)amino, $C_2$-$C_4$alkoxycarbonyl, $C_1$-$C_2$haloalkyl, $C_1$-$C_2$haloalkoxy, or oxo.

12. The method of claim 1, wherein Q is a $C_1$-$C_3$ hydrocarbon linking group.

13. The method of claim 1, wherein $R^1$ is hydrogen, fluoro, $C_1$-$C_3$alkyl, $C_1$-$C_3$alkoxy, $C_1$-$C_3$haloalkyl, $C_1$-$C_3$haloalkoxy, or aryl.

14. The method of claim 1, wherein $R^1$ is hydrogen, $C_1$-$C_2$alkyl, $C_1$-$C_2$alkoxy, $C_1$-$C_2$haloalkyl, or $C_1$-$C_2$haloalkoxy.

15. The method of claim 1, wherein $R^1$ is methyl or trifluoromethyl.

16. The method of claim 1, wherein $X^1$ is N.

17. The method of claim 1, wherein each instance of $R^3$ is halogen.

18. The method of claim 1, wherein G is

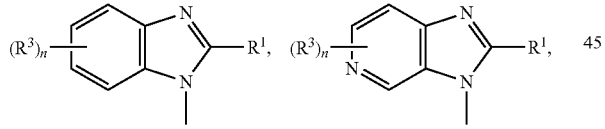

-continued

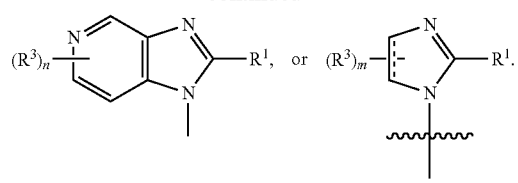

19. The method of claim 7, wherein Q is a $C_1$-$C_3$ hydrocarbon linking group substituted by 0, 1, 2, or 3 substituents independently chosen from hydroxy, amino, halogen, $C_1$-$C_2$alkyl, $C_3$-$C_5$cycloalkyl, $C_1$-$C_2$alkoxy, mono- and di-($C_1$-$C_2$alkyl)amino, $C_2$-$C_4$alkoxycarbonyl, $C_1$-$C_2$haloalkyl, $C_1$-$C_2$haloalkoxy, or oxo.

20. The method of claim 7, wherein Q is a $C_1$-$C_3$ hydrocarbon linking group.

21. The method of claim 7, wherein $R^1$ is hydrogen, fluoro, $C_1$-$C_3$alkyl, $C_1$-$C_3$alkoxy, $C_1$-$C_3$haloalkyl, $C_1$-$C_3$haloalkoxy, or aryl.

22. The method of claim 7, wherein $R^1$ is hydrogen, $C_1$-$C_2$alkyl, $C_1$-$C_2$alkoxy, $C_1$-$C_2$haloalkyl, or $C_1$-$C_2$haloalkoxy.

23. The method of claim 7, wherein $R^1$ is methyl or trifluoromethyl.

24. The method of claim 7, wherein $X^1$ is N.

25. The method of claim 7, wherein each instance of $R^3$ is halogen.

26. The method of claim 7, wherein G is

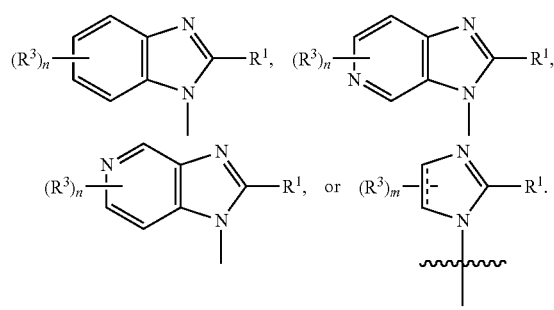

* * * * *